United States Patent [19]

Hamamoto et al.

[11] 4,376,080
[45] Mar. 8, 1983

[54] PROCESS FOR PREPARING MALONONITRILE

[75] Inventors: Toshikazu Hamamoto; Katsumasa Harada, both of Ube, Japan

[73] Assignee: Ube Industries, Ltd., Ube, Japan

[21] Appl. No.: 324,424

[22] Filed: Nov. 24, 1981

[30] Foreign Application Priority Data

Dec. 2, 1980 [JP] Japan ............................ 55-169162
Mar. 2, 1981 [JP] Japan .............................. 56-28333

[51] Int. Cl.³ .................. C07C 120/00; C07C 121/22
[52] U.S. Cl. ............................................. 260/465.8 R
[58] Field of Search ................................ 260/465.8 R

[56] References Cited

U.S. PATENT DOCUMENTS 4,126,610 11/1978 Belfort ..................... 260/465.8 R X
4,230,634 10/1980 Benzie et al. ............ 260/465.8 R X

FOREIGN PATENT DOCUMENTS 49-4207 1/1974 Japan ............................ 260/465.8 R
50-32125 3/1975 Japan ............................ 260/465.8 R

*Primary Examiner*—Joseph Paul Brust
*Attorney, Agent, or Firm*—Frishauf, Holtz, Goodman & Woodward

[57] ABSTRACT

Disclosed is a process for preparing malononitrile which comprises reacting diazoacetonitrile with hydrogen cyanide in the presence of a copper compound in a solvent. The diazoacetonitrile may be formed in a reaction mixture by reacting aminoacetonitrile with nitrous acid in a solvent, which is then subjected to the further reaction as such without isolating it from the reaction mixture.

20 Claims, No Drawings

PROCESS FOR PREPARING MALONONITRILE

This invention relates to a novel process for preparing malononitrile which is an important substance as a starting material for vitamin $B_1$.

As the process for preparing malononitrile, there have been heretofore proposed the following ones.
  (1) The process wherein monochloroacetic acid is reacted with sodium cyanide, the resulting cyanoacetic acid is esterified and aminated and then the resulting cyanoacetamide is dehydrated with phosphorus pentachloride.
  (2) The process wherein hydrogen cyanide is reacted with chlorine and the resulting cyanogen chloride is reacted with acetonitrile.

However, the process (1) involves an extremely long synthetic route. On the other hand, the process (2) involves need for a very high reaction temperature of about 900° C., formation of decomposed by-products in a large amount from acetonitrile and complicated procedures for isolating the desired product from the reaction system. Moreover, both processes (1) and (2) have drawbacks that the yield of the desired product is not so high as to be satisfactory and special equipment should be required for corrosion inhibition because of chlorine-containing substances applied.

The present invention have made intensive studies in order to establish a commercially advantageous process for preparing malononitrile. As a result, it has been found that malononitrile can be very advantageously prepared in a commercial scale by reacting diazoacetonitrile with hydrogen cyanide in the presence of a copper compound in a solvent, upon which this invention has been accomplished.

According to the present invention, there is provided a process for preparing malononitrile which comprises reacting diazoacetonitrile with hydrogen cyanide in the presence of a copper compound in a solvent. The diazoacetonitrile to be reacted with the hydrogen cyanide may be isolated in advance, or, preferably, a reaction mixture in which the diazoacetonitrile has been formed in a dissolved state in a solvent may be subjected to the reaction as such without isolating it therefrom. More particularly, a reaction mixture in which the diazoacetonitrile has been formed by reacting aminoacetonitrile with nitrous acid in a solvent under a condition of pH 10 or less may be subjected to the reaction as such without isolating it therefrom, with the hydrogen cyanide in the presence of a copper compound.

The present invention will be described below in more detail:

The starting material, diazoacetonitrile, in the present invention is an explosive, unstable substance, which is difficult to handle, but there is no such danger at all when placed in a solvent, e.g. ether, methylene chloride and the like.

The diazoacetonitrile can be readily synthesized and utilized by reacting an aminoacetonitrile, which is an inexpensively and readily available precursor of glycine which is one of amino acids commercially available in a large amount, with nitrous acid in an acidic aqueous medium and then extracting with a solvent, e.g. ether, methylene chloride and the like. What is to be noted here is that the solvent employed for the step for synthesizing the starting material, i.e. diazoacetonitrile, may be also suitable for the reaction step for obtaining the final product, whereby it is possible to make common completely or partly the solvent of the former step and that of the latter step. Thus, the reaction mixture resultant from former step in which the diazoacetonitrile is formed may preferably be applied to the latter reaction step as such without isolating the diazoacetonitrile from the reaction mixture, thereby omitting a step for isolating the starting material and also eliminating completely the danger in handling the same.

Accordingly, in the present invention, the diazoacetonitrile formed in the reaction mixture by reacting aminoacetonitrile with nitrous acid in a solvent may be subjected as such without isolating it therefrom, to the subsequent reaction with hydrogen cyanide in the presence of a copper compound.

The nitrous acid may be introduced into the reaction system in a gaseous state, but it is usually desirable to adopt such procedures wherein the nitrous acid is added to the reaction system in the form of a nitrous acid salt such as sodium nitrite, potassium nitrite or barium nitrite, or a nitrous acid ester such as ethyl nitrile, and then an acid or an acidic substance is added to the reaction system to form nitrous acid in situ.

The proportion of nitrous acid to aminoacetonitrile to be introduced into the reaction system is not particularly critical, but it is advisable to use nitrous acid in a slight excess amount for efficient reaction proceeding. However, in case of an overly excess amount of nitrous acid, an addition product may be formed by addition to the final product malononitrile and it is, therefore, desirable to control the proportion to a range of about 0.9~1.3 in terms of a molar ratio of nitrous acid-/aminoacetonitrile.

The reaction temperature in the above step is not particularly critical, but it is desirable in view of stability of the product and so on to use a temperature ranging $-10° \sim +20°$ C., most desirably $-10° \sim +10°$ C. When such a temperature is applied, the reaction is completed in about 0.5~3 hours.

The reaction of aminoacetonitrile with nitrous acid should be conducted with pH of the reaction mixture being maintained at 1~10. Particularly desirable pH range is 2~5. Further, when the nitrous acid salt or the nitrous acid ester is to be employed as a nitrous acid source, it is desirable to conduct the reaction by adjusting the pH of the reaction system to 2~5 through addition of an acid (usually, a weak acid such a phosphorus acid, acetic acid or oxalic acid) to the system.

The reaction mixture thus obtained may be subjected to the subsequent reaction as such or with some alteration of the solvent system. The term "some alteration of solvent system" is meant to include those procedures wherein the same solvent is further added to the resulting reaction mixture to lower a concentration of the diazoacetonitrile, wherein some part of the solvent in the said resulting reaction mixture is removed by distillation or other means, and wherein any solvent is added which has a high dissolving power for the diazoacetonitrile and/or the final reaction product (malononitrile).

If the concentration of diazoacetonitrile relative to the solvent is too high there would be danger of explosion. Accordingly, it is advantageous to adjust it so that not more than 30 parts by weight, preferably 1~15 parts by weight of diazoacetonitrile based on 100 parts by weight of the solvent may be contained in the solvent system.

The solvent which may be utilized for the present invention may be any of those which are inert to the reaction and may dissolve diazoacetonitrile or aminoacetonitrile and hydrogen cyanide. As examples thereof, there may be mentioned an aliphatic saturated hydrocarbon such as n-hexane or n-heptane, an aromatic hydrocarbon such as benzene or toluene, a cyclic saturated hydrocarbon such as cyclohexane, a halogenated hydrocarbon such as chloroform, methylene chloride, carbon tetrachloride, trichloroethylene, 1,2-dichloroethylene or 1,2-dichloroethane, an ether such as diethyl ether, dioxane, methyl cellosolve or ethyl cellosolve, an alcohol such as methanol, ethanol or isopropanol and water, etc. They may be employed usually alone, but may be used in admixture therewith. However, from an industrial standpoint, there may be used ethyl ether, methylene chloride, chloroform, carbon tetrachloride, n-hexane, water and the like, which are employed as an extract solvent in preparing diazoacetonitrile from aminoacetonitrile.

The manner to add hydrogen cyanide to the reaction system is not particularly critical. For instance, hydrogen cyanide may be added as such to the reaction system, or hydrogen cyanide may be produced in the reaction system per se by adding both of a sodium cyanide or potassium cyanide and an acid such as sulfuric acid, to the reaction system.

Hydrogen cyanide is preferably employed in an approximately equimolar amount or a slightly excess amount to diazoacetonitrile or aminoacetonitrile. Generally, the hydrogen cyanide is added in an amount of 0.8 to 1.5 mole per mole of diazoacetonitrile or aminoacetonitrile.

The copper compound which may be employed as a catalyst in this invention may be any of those copper-containing compounds, irrespective of being monovalent or divalent. There may be mentioned, for example, monovalent and divalent copper sulfates, copper carbonates, copper acetates, copper cyanides, copper perchlorates, copper chlorides and the like.

The copper compound may be advantageously employed at 0.001~2 gram-atoms, preferably 0.01~1 gram-atom in terms of metallic copper per mole of diazoacetonitrile or aminoacetonitrile.

The reaction may be carried out at a temperature of not more than 50° C., preferably 0°~40° C., for 0.5~5 hours, since diazoacetonitrile or aminoacetonitrile is apt to decompose or hydrogen cyanide tends to vaporize off when a too high temperature is applied.

The reaction is carried out under the pH condition of pH 3~12, preferably pH 4~11. When the step for synthesizing the diazoacetonitrile is conducted under a particularly low pH condition, suitable pH adjustment for the subsequent reaction is to be effected by addition of an alkaline agent or other suitable means.

Malononitrile, the final reaction product, is of a high solubility, especially, in an ether such as ethyl ether or isopropyl ether or a halogenated hydrocarbon such as methylene chloride or chloroform. Consequently, the product may be usually recovered in the dissolved state in such a solvent from the reaction mixture and then isolated. A major portion of by-products in this reaction step is assumed to be glycononitrile ($HOCH_2CN$), which is highly soluble in water. Then, malononitrile with a high purity can be obtained by treating the reaction mixture with a mixed system of water and the said organic solvent such as ethers or halogenated hydrocarbons so that the by-products may remain in water, while malononitrile may be extracted into the organic solvent phase. Moreover, when water or such an organic solvent as ethers or halogenated hydrocarbons is used as the reaction solvent, the said reaction solvent may be utilized as the whole or part of a solvent for separation and extraction. By treating the reaction mixture with a mixed system of water and the said organic solvent having a high dissolving power for malononitrile (ethyl ether, methylene chloride and the like as set forth above), there can be obtained malononitrile with a purity of 98% or higher. Further examples of the organic solvent employable for the same purpose may include isopropanol, butanol and so on.

According to the present invention, there are gained, as explained hereinabove, advantages that malononitrile can be prepared from inexpensive, easily available starting materials using a comparatively simple and short process and the so produced malononitrile can be readily recovered in high purity so that subsequent purification is not generally required. As apparent from the foregoing, the process of the present invention is of excellent practical use as an industrial process for manufacturing malononitrile, as compared with the prior art process.

Examples of this invention and a Comparative Example are given below. In the Examples, all yields of malononitrile are on the basis of diazoacetonitrile or aminoacetonitrile.

EXAMPLE 1

To 140 g. of a methylene chloride solution of 3.3 g. of diazoacetonitrile was added an aqueous solution of 1.8 g. of hydrogen cyanide in 10 g. of water and the resulting solution was kept at 10° C. Thereafter, to the solution were added over 15 minutes 10 ml. of an aqueous solution of 0.3 g. of cupric sulfate and the reaction was carried out at 10°~20° C. for 2 hours.

After completion of the reaction, the aqueous layer and the organic layer were separated and the malononitrile dissolved in a small amount in the aqueous layer was extracted four times with 50 ml portions of diethyl ether. The extract and the previously separated organic layer were mixed and dehydrated with calcium chloride and the solvent was distilled off to afford 3.1 g of malononitrile. Yield, 93.0% based on diazoacetonitrile.

EXAMPLES 2~5

Experiments were effected by the same procedures as in Example 1 except that various copper compounds were employed in the pre-determined amounts instead of the cupric sulfate.

Comparative Example

Experiment was effected by the same procedures as in Example 1 except that the cupric sulfate was not employed.

Results from Examples 1~5 and Comparative Example are shown in the following Table 1.

TABLE 1

| | Copper compound | | Yield of malono-nitrile |
|---|---|---|---|
| | Type | Amount used (g) | |
| Ex. | | | |
| 1 | Cupric sulfate | 0.2 | 93.0 |
| 2 | Cupric acetate | 0.5 | 90.0 |
| 3 | Cupric chloride.2 hydrate | 0.2 | 73.3 |
| 4 | Cuprous cyanide | 0.2 | 79.0 |
| 5 | Cuprous chloride | 0.15 | 85.7 |

TABLE 1-continued

| | Copper compound | | Yield of malononitrile |
|---|---|---|---|
| | Type | Amount used (g) | |
| Comp. Ex. | None | | 5.0 |

EXAMPLE 6

An aqueous solution containing hydrogen cyanide and sodium sulfate was prepared by mixing with stirring 24.5 g. of a 10% by weight aqueous solution of sodium cyanide and 4.9 g. of a 50% by weight aqueous solution of sulfuric acid. This aqueous solution was added to 140 g. of a methylene chloride solution of 3.3 g. of diazoacetonitrile and the resulting solution was kept at 10° C. Then, to this solution were added over 15 minutes 10 ml. of an aqueous solution of 0.3 g. of cupric sulfate and the reaction was carried out at 10°~20° C. for 2 hours.

Subsequent procedures were conducted in the same manner as in Example 1 to afford 2.9 g. of malononitrile. Yield, 89% based on diazoacetonitrile.

EXAMPLE 7

To 68.8 g. of a mixture of methylene chloride-carbon tetrachloride (1:1 by volume) having dissolved therein 1.3 g. of diazoacetonitrile was added a solution prepared by neutralization of 29.4 g. of a 5% by weight aqueous sodium cyanide solution with 2.2 g. of acetic acid and the resulting mixture was kept at 10° C. Then, to this solution were added over 15 minutes 10 ml. of an aqueous solution of 0.4 g. of cupric sulfate and the reaction was carried out at 10°~20° C. for 2 hours.

Subsequent procedures were conducted in the same manner as in Example 1 to give 1.1 g. (yield 87.3%) of malononitrile with 0.16 g. of unreacted diazoacetonitrile being found.

EXAMPLE 8

In a three neck flask, a solution of 5.25 g. (0.05 mole) of aminoacetonitrile sulfate ($NH_2CH_2CN.\frac{1}{2}H_2SO_4$) in 50 ml. of water was kept at 2° C. and then a solution of 3.5 g. (0.05 mole) of sodium nitrite in 25 ml. of water was added thereto within 10 minutes while keeping the temperature below 5° C. Then, a solution of 2.7 g. of acetic acid in 25 ml. of water was slowly added thereto over one hour to adjust pH of the resulting solution to about 2. After completion of the addition, slow stirring was continued at 0° C. for further one hour, whereupon pH of the reaction mixture rose to about 4. After completion of the reaction, the reaction mixture was adjusted to pH 6.5 by the addition of sodium carbonate. Thereafter, 25 ml. of an aqueous solution of 2 g. (0.075 mole) of hydrogen cyanide were added thereto together with 25 ml. of an aqueous solution containing 0.4 g. of cupric sulfate and vigorous stirring was done at 10°~20° C. for 2 hours. The reaction mixture was extracted four times with 150 ml. portions of ethyl ether and there were obtained from the extract 2.31 g. (0.0351 mole) of malononitrile. Yield, 70.2% based on aminoacetonitrile.

EXAMPLE 9

In a three neck flask, 15 ml. of an aqueous solution of 52.5 g. (0.05 mole) of aminoacetonitrile sulfate ($NH_2CH_2CN.\frac{1}{2}H_2SO_4$) and 50 ml. of ethyl ether were added and kept at 2° C. Then, 10 ml. of an aqueous solution of 3.5 g. (0.051 mole) of sodium nitrite were added thereto within 10 minutes while keeping a temperature of the reaction mixture below 5° C. Further, 3.6 g. (0.06 mole) of acetic acid were added thereto over one hour to adjust pH of the solution to about 2. Thereafter, the reaction was effected in the same manner as in Example 8, whereupon pH of the reaction mixture rose to about 4. Subsequent pH adjustment and reaction with hydrogen cyanide were conducted in the same manner as in Example 8 and, after completion of the reaction, the ether layer was separated and the aqueous phase was extracted three times with 50 ml. portions of ethyl ether and the ethyl ether layer was separated. From the combined ether layers, there were obtained 2.24 g. (0.034 mole) of malononitrile. Yield, 68% based on aminoacetonitrile.

EXAMPLE 10

The same procedures as in Example 9 were carried out by employing 4.1 g. (0.059 mole) of sodium nitrite, 90 ml. of methylene chloride instead of the ethyl ether and 1.2 g. (0.0125 mole) of phosphoric acid instead of the acetic acid.

From a mixture of methylene chloride-ethyl ether, there were obtained 2.58 g. (0.039 mole) of malononitrile. Yield, 78% based on aminoacetonitrile.

We claim:

1. A process for preparing malononitrile which comprises reacting, in a solvent and at a pH between 3 and 12, diazoacetonitrile with hydrogen cyanide in the presence of between 0.001 and 2 gram-atoms of a copper compound in terms of metallic copper per mole of said diazoacetonitrile, said copper compound being selected from the group consisting of monovalent or divalent copper sulfate, copper carbonate, copper acetate, copper cyanide, copper perchlorate and copper chloride.

2. The process according to claim 1, wherein the reaction is carried out at a temperature ranging from 0° to 50° C.

3. The process according to claim 1 or 2, wherein said hydrogen cyanide is added in an amount of 0.8 to 1.5 mole per mole of said diazoacetonitrile.

4. The process according to claim 1 or 2, wherein said solvent is at least one selected from the group consisting of ethyl ether, methylene chloride, chloroform, carbon tetrachloride, n-hexane and water.

5. The process according to claim 3, wherein said pH is 4 to 11.

6. The process according to claim 1, wherein said diazoacetonitrile is formed in a reaction mixture by reacting aminoacetonitrile with nitrous acid in a solvent under a condition of pH 1 to 10, which is then reacted with said hydrogen cyanide as such without isolating it from the reaction mixture.

7. The process according to claim 6, wherein the proportion of said nitrous acid to said aminoacetonitrile ranges from 0.9 to 1.3 in terms of a molar ratio of nitrous acid/aminoacetonitrile.

8. The process according to claim 6 or 7, wherein the reaction of aminoacetonitrile with nitrous acid is carried out at a temperature ranging from −10° to +20° C.

9. The process according to claim 6 or 7, wherein said hydrogen cyanide is added in an amount of 0.8 to 1.5 mole per mole of aminoacetonitrile.

10. The process according to claim 6 or 7, wherein said solvent is at least one selected from the group consisting of ethyl ether, methylene chloride, chloroform, carbon tetrachloride, n-hexane and water.

11. The process according to claim 6 or 7, wherein the reaction of aminoacetonitrile with nitrous acid is carried out under a condition of pH 2 to 5.

12. The process according to claim 8, wherein said hydrogen cyanide is added in an amount of 0.8 to 1.5 mole per mole of aminoacetonitrile.

13. The process according to claim 8, wherein said solvent is at least one selected from the group consisting of ethyl ether, methylene chloride, chloroform, carbon tetrachloride, n-hexane and water.

14. The process according to claim 9, wherein said solvent is at least one selected from the group consisting of ethyl ether, methylene chloride, chloroform, carbon tetrachloride, n-hexane and water.

15. The process according to claim 12, wherein said solvent is at least one selected from the group consisting of ethyl ether, methylene chloride, chloroform, carbon tetrachloride, n-hexane and water.

16. The process according to claim 8, wherein the reaction of aminoacetonitrile with nitrous acid is carried out under a condition of pH 2 to 5.

17. The process according to claim 15, wherein the reaction of aminoacetonitrile with nitrous acid is carried out under a condition of pH 2 to 5.

18. The process according to claim 3, wherein said solvent is at least one selected from the group consisting of ethyl ether, methylene chloride, chloroform, carbon tetrachlorine, n-hexane and water.

19. The process according to claim 18, wherein said pH is 4 to 11.

20. The process according to claim 17, wherein the reaction of said diazoacetonitrile with hydrogen cyanide is carried out at a temperature between 0° and 50° C. and at a pH between 4 and 11, wherein said hydrogen cyanide is in an amount between 0.8 and 1.5 mole per mole of said diazoacetonitrile, and wherein the solvent for said reaction is the same solvent in which said diazoacetonitrile is formed.

* * * * *